United States Patent
Hall et al.

(10) Patent No.: US 6,918,766 B1
(45) Date of Patent: Jul. 19, 2005

(54) METHOD, ARRANGEMENT AND USE OF AN IMPLANT FOR ENSURING DELIVERY OF BIOACTIVE SUBSTANCE TO THE BONE AND/OR TISSUE SURROUNDING THE IMPLANT

(75) Inventors: Jan Hall, Göteborg (SE); Lennart Lööf, Västra Frölunda (SE)

(73) Assignee: Nobel Biocare Ab (SE)

( * ) Notice: Subject to any disclaimer, the term of this patent is extended or adjusted under 35 U.S.C. 154(b) by 0 days.

(21) Appl. No.: 09/980,009
(22) PCT Filed: May 23, 2000
(86) PCT No.: PCT/SE00/01029
§ 371 (c)(1),
(2), (4) Date: Feb. 28, 2002
(87) PCT Pub. No.: WO00/72778
PCT Pub. Date: Dec. 7, 2000

(30) Foreign Application Priority Data

May 31, 1999 (SE) ............................. 9901972

(51) Int. Cl.⁷ ............................. A61C 8/00; A61F 13/00
(52) U.S. Cl. ..................... 433/201.1; 433/174; 424/435
(58) Field of Search .......................... 604/890.1, 891.1; 424/422, 423, 434, 435; 433/80, 81, 82, 201.1, 173, 174

(56) References Cited

U.S. PATENT DOCUMENTS

| | | | | |
|---|---|---|---|---|
| 4,175,326 A | * | 11/1979 | Goodson | 433/80 |
| 4,685,883 A | * | 8/1987 | Jernberg | 433/215 |
| 4,744,755 A | * | 5/1988 | Ross | 433/173 |
| 4,764,377 A | * | 8/1988 | Goodson | 424/435 |
| 4,959,052 A | * | 9/1990 | Cox | 604/77 |
| 4,994,273 A | * | 2/1991 | Zentner et al. | 424/422 |
| 5,059,123 A | * | 10/1991 | Jernberg | 433/215 |
| 5,458,884 A | * | 10/1995 | Britton et al. | 424/435 |
| 5,496,559 A | * | 3/1996 | Fujioka et al. | 424/435 |
| 5,700,479 A | * | 12/1997 | Lundgren | 424/435 |
| 5,702,695 A | * | 12/1997 | Clokie | 424/78.08 |
| 6,132,214 A | * | 10/2000 | Suhonen et al. | 433/201.1 |
| 6,413,089 B1 | * | 7/2002 | Ashman et al. | 433/174 |
| 6,530,896 B1 | * | 3/2003 | Elliott | 604/60 |
| 2001/0004711 A1 | * | 6/2001 | Lazzara et al. | 623/23.5 |
| 2003/0003128 A1 | * | 1/2003 | Chiarelli | 424/423 |
| 2004/0053196 A1 | * | 3/2004 | Mayer et al. | 433/173 |
| 2004/0209228 A1 | * | 10/2004 | Ilan | 433/201.1 |

* cited by examiner

*Primary Examiner*—Sharon Kennedy
(74) *Attorney, Agent, or Firm*—Connolly, Bove, Lodge & Hutz LLP

(57) ABSTRACT

In connection with implants for bone or tissue, delivery of bioactive substances to the bone or tissue is ensured. The implant is designed with an internal space, and one or more bodies comprising the bioactive substance are designed to cooperate with the bone and/or tissue structure surrounding the implant and to release the bioactive substance to the said structure. The said body or bodies is/are applied in the space in order thereby to be exposed to the surrounding structure and deliver the bioactive substrate or substances to the latter.

18 Claims, 3 Drawing Sheets

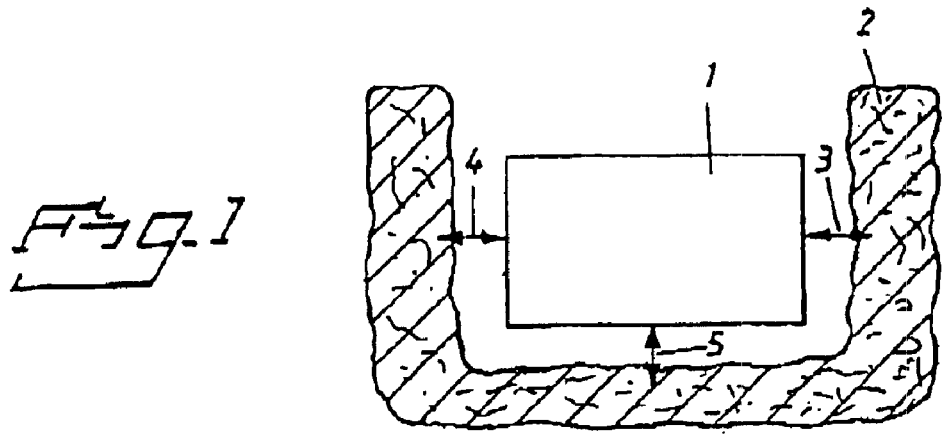
FIG. 1
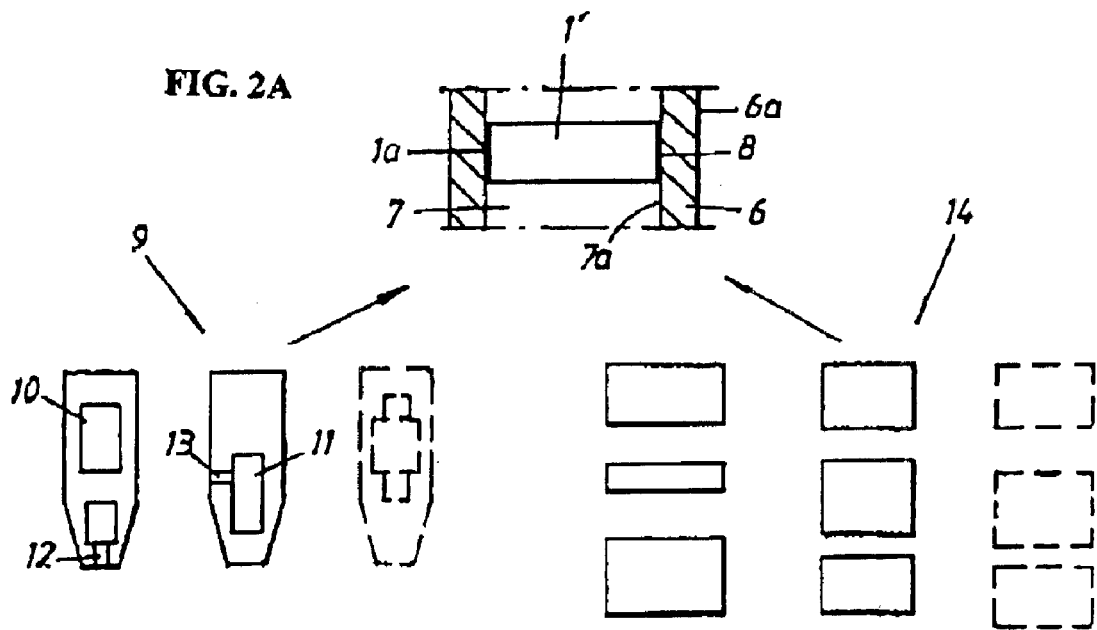
FIG. 2A
FIG. 2B
FIG. 2C
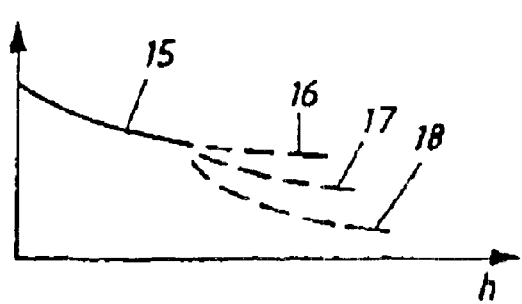
FIG. 3

Fig. 6
Fig. 7
Fig. 8
Fig. 9
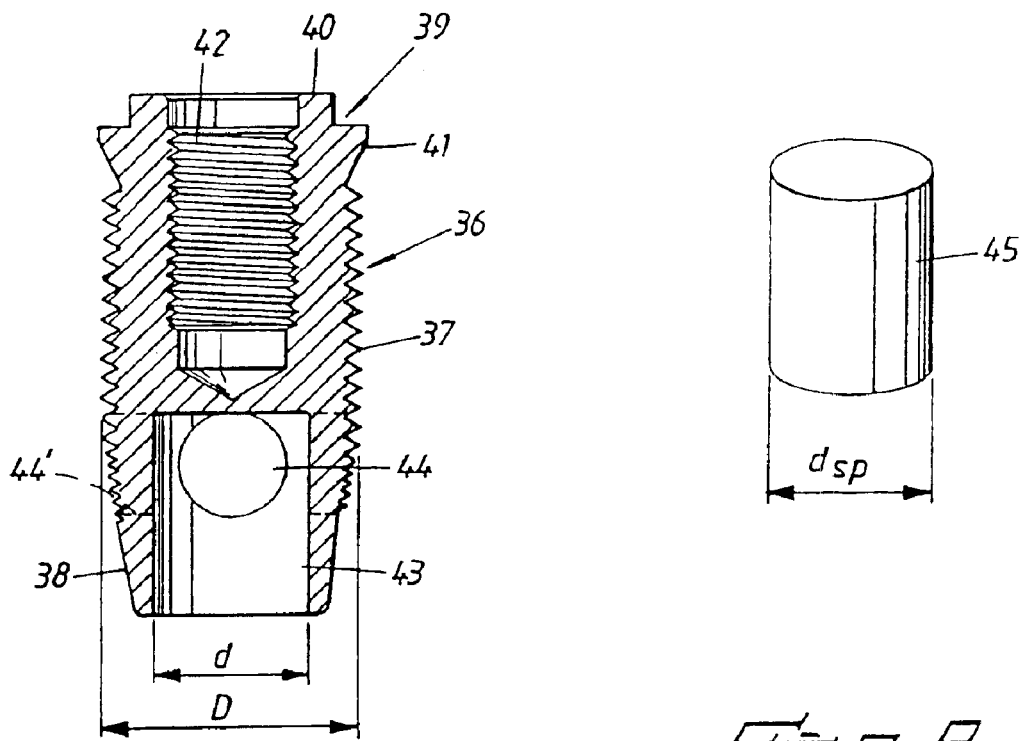
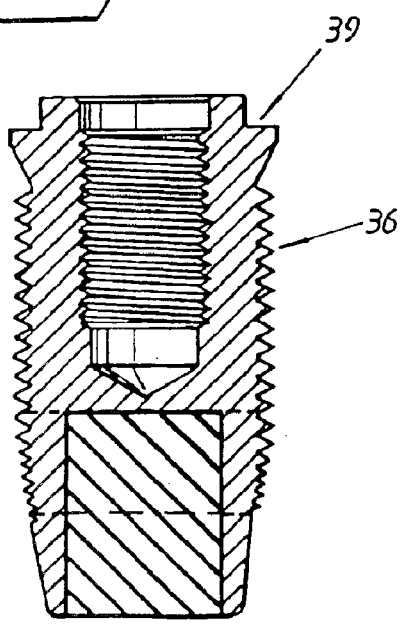
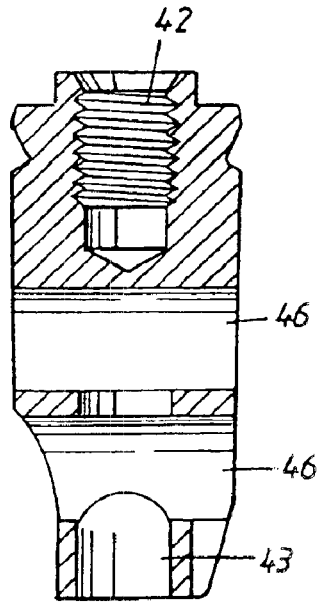

METHOD, ARRANGEMENT AND USE OF AN IMPLANT FOR ENSURING DELIVERY OF BIOACTIVE SUBSTANCE TO THE BONE AND/OR TISSUE SURROUNDING THE IMPLANT

TECHNICAL FIELD

The present invention relates to a method for use in connection with an implant for bone and/or tissue structure, for example dentine, and ensuring delivery of bioactive substance to the structure during all or part of the period of incorporation of the implant. The invention also relates to an arrangement and use of such an implant and such delivery.

PRIOR ART

In connection with implants, it is already known to use various types of bioactive substances intended to improve the incorporation of the implant in the bone or tissue in question. Thus, for example, it may be desirable to use a substance belonging to the superfamily TGF-β, for example so-called BMP (Bone Morphogenetic Proteins) in order to initiate and stimulate bone growth. Reference may be made here to patent publications WO 95/33502, WO 96/40014 and WO 98/17330, among others.

Implants and implant elements and methods for permanent anchoring in mineralized tissue have been known for a long time. To prevent the implant from coming loose, it is important to establish direct contact (i.e. direct application) between the outer surface of the implant or implant element and the surrounding body tissue. When direct application has indeed been established, the implant is stable, and so-called osseointegration can be obtained. Direct contact between the surface of the implant element and the bone tissue can be obtained by means of a suitable implant structure and refined surgical technique. The principle of osseointegration has been developed by Professor Bránemark et al. and has been used successfully in the treatment of edentulous patients with dental implants for many years.

The treatment of edentulous patients usually includes careful patient selection, a detailed surgical protocol, and careful planning of the prosthetic constructions which are to be used. The most successful clinical results have been achieved after treatment of patients with tight, compact bone in which it is fairly easy to obtain stable fixation of the implant. However, less successful results have been reported after treatment in bone of softer quality. The difficulties have manifested themselves in the break-up of a stable implant fixation. Various methods have been proposed to overcome these difficulties. These methods generally involve using additional new means for implant surfaces, for example coating with hydroxyapatite, or preparation of implant surface irregularities which have been judged to improve the implant fixation. Very little is in fact known of the relative importance of implant geometry, chemical surface properties and surface irregularities. However, implant geometry probably plays an important role, since it has a strong influence on the load distribution in the tissue surrounding the implant body.

Running parallel with the development of different types of implants, investigations have been conducted with the aim of characterizing the interaction of cells and cellular molecules in living tissue. Detailed analysis of the interaction at the cellular and molecular level has been found to be fundamental for the development of the modern pharmaceutical industry and genetic engineering. However, such knowledge could also be successfully used in the development of load-bearing implants in bone. When the mechanisms of interaction are known, it may be possible to act on the processes of interaction and the possibilities of stimulating bone growth and increasing bone density and bone volume in or at the implant site in the body. This is often a precondition for stable implant fixation in less than optimal circumstances with soft bone qualities.

A particular example of acting on bone growth and increasing bone density is the use, as mentioned above, of bioactive substances. Growth factors can stimulate bone growth in a known manner, provided that they are released into the surrounding tissue at a sufficient concentration and speed for a fairly long period of time after their introduction.

Insofar as reference is made to the said Bránemark system, reference may also be made, inter alia, to European Patent Application 95102381.1 (676179).

Implants as such are already very well known and are commercially available in large numbers and in many different ranges. Implants which are relevant in this context are disclosed, for example, in U.S. Pat. No. 4,960,301, as well as implants which are shown in the publication "Oral Implantology" which relates to "ITI Hollow Cylinder System", published 1991 by Georg Thieme Verlag, Stuttgart and New York.

Studying and/or acting on the anchoring of implants in living biological tissues under variable conditions, especially in the form of reaction to locally applied substances, is the subject of European Patent Specification 720833. This arrangement comprises an anchoring element which is to be incorporated in the tissue. It has a central recess in the form of a depot for the substance in question. The surface of the anchoring element adjoining the tissue consists entirely or partially of penetrable material or "filter" which allows the applied substance to diffuse out onto the implant surface, or into the biological fluid around the implant surface, from a central recess. Although it is stated that such an anchoring element would simulate clinically produced implants with respect to material and/or surface properties, implantation positions and surgical technique, it must be appreciated that this type of anchoring element, with its depot for providing the substance and with a separate filter element, is less attractive for permanent anchoring when it is used as a conventional implant element. Specifically, the introduction of the active substance in solid form or liquid form in a specific depot and a filter element, through which the active substance is allowed to diffuse, is less suitable and means that this type of implant arrangement is more suited for test purposes than for long-term clinical use.

DESCRIPTION OF THE INVENTION

Technical Problem

In connection with implants of the type in question, it is important to establish an appropriate substance layer function at and in connection with the implant. The main object of the invention is to solve this problem, among others.

It is important to be able to use tried and tested experience with proven and effective implant structures without essentially affecting these in other respects. The invention solves this problem too.

In connection with clinically well-designed implants, it is important to be able to achieve an effective use and release function for the bioactive substance in question, all of which substance must be able to be used effectively. In various designs, it is also important to be able to control the release function during the incorporation process, for example so that an initially high release function is available during a first time period and a lower release function is obtained during a second time period, or vice versa. The variations in question must be able to be effected by choice of differently structured implants in terms of the support function for the bioactive substance arranged in the respective implant. The invention solves this set of problems too.

One object of the invention is thus to combine the properties of clinically efficient implant elements and clinically efficient supports for growth factors, by modifying the geometry of existing implant elements in order to obtain secure containment of the substance in the element. Such a novel implant element can permit rapid incorporation of surrounding tissue and stable fixation even in non-optimal bone qualities, and it does this by virtue of the stimulation activity from the growth factors which are released from the support or body.

A further object of the invention is to make available an implant element with an external structure which is similar to or corresponds to the clinically efficient implant elements, so-called fixtures, which permit positioning of efficient supports or bodies with respective growth factors and a sought release of these growth factors into the tissue which is stored in the body of the implant element. Such a combination of implant element and support permits stimulation of bone growth in the tissue surrounding the implant element and also rapid incorporation and stable fixation of the implant elements in mineralized tissue.

SOLUTION

The features which can principally be regarded as characterizing a method according to the invention are that the implant is designed with an internal space and, if appropriate, one or more channels and/or recesses leading from the internal space to the outside or outside part of the implant facing towards the structure, that one or more bodies comprising the bioactive substance are designed to cooperate with the bone and/or tissue structure surrounding the implant so as to be able to release the bioactive substance to the said surrounding structure. Further characteristics are that the said body or bodies is/are applied in the said space and, if appropriate, also in one or more of the said channels and/or recesses, in order thereby to be exposed to the said surrounding structure and deliver the bioactive substance to the latter during the said period.

An arrangement according to the invention can principally be regarded as being characterized in that the implant is designed with one or more internal spaces and, if appropriate, one or more channels or recesses which lead from the internal space or spaces to the outside of the implant. Further characteristics are that one or more bodies comprising the bioactive substance are designed to cooperate with the surrounding bone and/or tissue structure so as to release the bioactive substance to the surrounding structure, and that the body or bodies is/are assigned a position or positions in the space or spaces in which they are exposed for the said cooperation and release directly or via the said channel(s) or recess(es).

In one embodiment, each body is in the form of a spongy body or cloth saturated in or treated with the bioactive substance. Alternatively, the body can be in the form of a gel which comprises the bioactive substance. The spongy body, the cloth or the gel has a softness which permits distinct application in the space concerned while at the same time ensuring that it is held in place by frictional cooperation, adhesive cooperation, etc., with the wall of the respective space. In a preferred embodiment, the implant or implant element has clinically effective geometrical properties, for example in the shape of a cylindrical or conical solid with an outer surface which is in direct contact with the surrounding body tissue.

The bioactive substance can be a substance belonging to the superfamily TGF-$\beta$. In a preferred embodiment, the implant element has a threaded outer surface and a conically narrowing part. The latter part has an open section with an axial hole or recess for the said support or body. The hole or recess is open towards the end surface of the conical part. One or more through-holes communicate with the said axial holes and extend radially through the implant body part at right angles to the longitudinal axis of the implant in order to permit direct release of bioactive substance from the said support through the said holes or openings.

The internal space in question can thus comprise a mouth part or recess part with identical cross-sectional areas, and the body or support can fill both the internal space and the recess.

In one embodiment, the said axial hole can extend from the conical part through the main part of the implant body in order to permit release of growth factors along the length of the implant body through a suitable number of holes, channels and/or recesses in the wall of the implant element. The design and structure of the body/support or bodies/supports are chosen on the basis of a predetermined or anticipated release function. A first body can assume a first position in which the first body is arranged with a first degree of exposure, and a second body assumes a second position in which the second body has a second degree of exposure less than the first degree of exposure, or vice versa, for the purpose of permitting a controlled or optimum release function for the bioactive substance in question.

Alternatively, each body can be arranged in such a way that, in the said cooperation and release function, it varies the degree of release of the bioactive substance during the release period and, for example, effects a greater degree of release at the start of the period, or vice versa. In a further embodiment of the element, the design(s) or extent(s) of the space or spaces and any associated channels or recesses are chosen on the basis of a predetermined or anticipated release function. The channels or recesses can be arranged with different cross-sectional areas and/or extents, which means that different parts of the same body or different bodies are subject to different degrees of exposure in the release function, for the purpose of permitting a controlled or optimum release function for the implant situation in question. In a further embodiment, two bodies can be situated at a distance from each other inside the implant or implant element in order to serve different parts of the surrounding bone and/or tissue structure. The body can be absorbable in association with the release of substance. The body (bodies) can first be applied in the space and thereafter saturated with substance, which saturation can be effected with substance at different concentrations and/or quantities for the purpose of achieving a predetermined or anticipated release function.

A use according to the invention can principally be regarded as being characterized in that the implant is used to support, in one or more internal spaces, one or more bodies comprising the bioactive substance, and, via possible attachments to the space or spaces, to expose the body or bodies in order to release the bioactive substance to the surrounding bone and/or tissue structure.

Advantages

By means of what has been proposed above, a novel aid is obtained for use in surgery for the purpose of obtaining effective incorporation processes in tissue, for example bone tissue. An implant according to the invention, provided with support(s) or body (bodies), can be made commercially available. Alternatively, the implant and support/body/bodies can be made available separately and joined together in situ by the person concerned, for example the surgeon. Various types of supports with different release functions and release times can be included within one range. Various types of implants or implant elements with different systems of channels and internal spaces can be made available in order to permit different release functions and release times. In addition, each body can be saturated with substance in a different quantity and/or concentration. Well-proven surgical procedures, substances and implant designs can be used in different implantation situations, which can include implantation in hard or soft dentine.

DESCRIPTION OF THE FIGURES

A presently proposed embodiment of a method, arrangement and use according to the present invention will be described below with reference to the attached drawings, in which FIG. 1 shows, in vertical section, the cooperation between bioactive substance, included in a body or support, and bone tissue which is shown diagrammatically and in which biological organisms and fluids are present, FIGS. 2A–2C show, in block diagram form, the production of an implant with body or support with bioactive substance, chosen from a range of differently constructed implants and a range of differently constructed bodies/supports designed with different release functions.

FIG. 3 shows a time diagram of the release function for implants with different supports, FIG. 6 shows, in vertical section, a first structural design of an implant with internal space for body/support, FIG. 7 shows, in perspective and obliquely from above, a body or support with growth factors which is intended to be inserted into an implant according to FIG. 7, FIG. 8 shows, in vertical section, the implant according to FIG. 7, but turned through 90° in relation to FIG. 7, and FIG. 9 shows, in vertical section, a second design of an implant.

DETAILED EMBODIMENT

Figure 4:
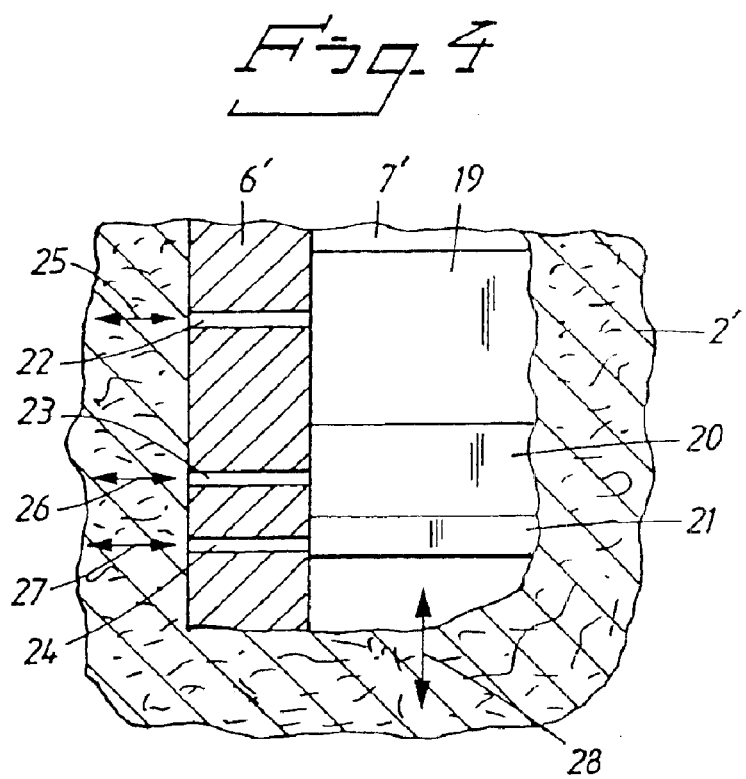
FIG. 4 shows, in vertical section, a first system of channels and internal spaces in an implant, and bodies/supports arranged in the latter.

In FIG. 1, a support for bioactive substance in accordance with the above is indicated by reference number 1. The body or support 1 can be in the form of a sponge which is saturated with the said bioactive substance. Alternatively, the support or body can comprise a gel. The body or support is shown separately (i.e. without implant) in relation to a surrounding bone and/or tissue structure which has been symbolized by 2. The body must be of such a type that it can cooperate with the structure 2 so that its bioactive substance can be released to the surrounding structure 2 in question. The release function is initiated by the biological organisms and fluids of the structure. It may also be assumed that the bioactive substance introduced into the body or support 1 or applied onto the body or support causes, by virtue of its high concentration, a concentration diffusion across to the structure. In the figure, the said cooperation is shown by dual-direction arrows 3, 4 and 5. The cooperation between the bioactive substance and the structure may be assumed to work in both directions.

FIGS. 2A–2C reference number 6 indicates an implant or implant element, into which a body or support 1' with bioactive substance is inserted. The body is spongy or soft and can be pressed into the recess of the implant in question, which recess is indicated by 7. A distinct and clear position of the body 1' in the recess 7 can he obtained by means of friction between the outside 1a or outer surface of the body 1 and the inner wall 7a of the recess. In addition to this, or alternatively, a securing means, for example an adhesive paste 8, can be used. The implant 1' is chosen from a range of implants, which range is indicated by 9. In the range of implants, the various implants have different designs, for example different internal spaces 10, 11 and different systems of channels or recesses 12, 13. The body or support 1' is chosen from a range of bodies or supports, which range is indicated by 14. The bodies or supports can be designed for different release functions for bioactive substances applied on the bodies. Likewise, the system of channels and spaces can be arranged so that these give the respective body in the respective implant different degrees of exposure, for the purpose of producing different, controlled and/or optimal release times.

In FIG. 3, examples of the said release functions are shown in diagram form. The vertical axis shows the quantity of bioactive substance released, and the horizontal axis shows the time. Different curves 15 and curve combinations 16, 17 and 18 can be established on the basis of the said choices from the ranges 9 and 14. The outer surface of the implant is indicated by 6a.

FIG. 4 shows surrounding body tissue 2', and an implant which has been inserted into the tissue is indicated by 6'. The implant is designed with a space 7', and in this space there are three bodies/supports with bioactive substances, indicated by 19, 20 and 21. The bodies or supports communicate with the surrounding tissue 2' via channels 22, 23 and 24, respectively, and the cooperation with the surrounding tissue is indicated by 25, 26 and 27. The lowermost body 21 also cooperates, via a larger recess, with the surrounding tissue in the direction of the arrow 28.

Figure 5:
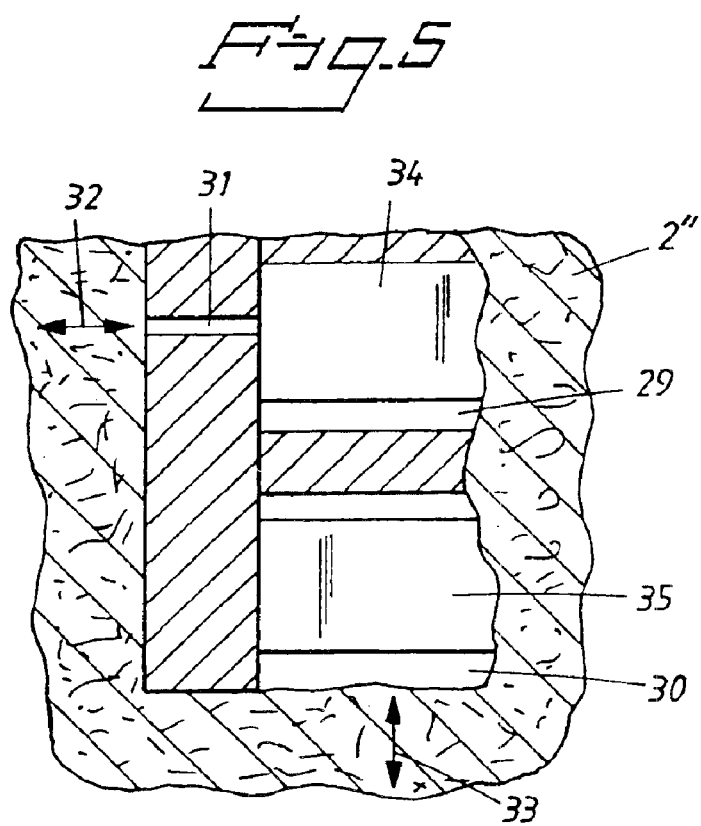
FIG. 5 shows, in vertical section, a second design of the internal spaces and channel system.

FIG. 5 illustrates the case where a number of spaces 29 and 30 are provided. The space 29 communicates with the tissue 2" via one or more channels 31, the cooperation being indicated by 32. The space 30 cooperates directly with the tissue 2' in the direction of arrow 33. The body in the space 29 is indicated by 34, and the body in the space 30 is indicated by 35.

The implant element according to FIG. 6 represents a modification of an implant fixture in the well-known Brånemark System® which consists of a general cylindrical, solid titanium body part with a threaded outer surface 37 and a conical end part 38. The implant fixture further consists of a head part 39 with an anti-rotation design in the form of a hexagon 40 which can be acted on using a suitable turning tool. The head part also consists of a smaller conical flange 41 and a central threaded inner hole 42 for the tightening screw (not shown) which extends along the longitudinal axis of the implant. The end part 38 has an open section which, in this example, comprises an axial hole or recess 43 which is open towards the end surface, and a through-hole 44 which communicates with the said hole 43 and extends radially through the implant body at right angles to the axis of the implant. As is indicated, a second through-hole 44' can also be formed in the body section such that the two holes are at right angles to each other.

The width dimension D of the body part of the implant fixture is in the range of 3.7 mm to 6.0 mm. In this illustrative embodiment, D is about 5.0 mm, and the length of the implant fixture is about 10 mm. The diameter d of the axial hole 43 is 3 mm, and the depth is 4 mm. The transverse hole 44 has a diameter of 2 mm, and the holes are drilled through the implant body. The threaded inner hole 42 for the Bránemark Systems implant fixture which is used in this particular example is 6 mm in depth along the implant axis. The inner hole 42 thus sets a limit for the maximum possible depth of the 3 mm axial hole 43.

Compared with the standardized Bránemark System® implant fixture, and also compared with other known implant fixtures of this type available on the market, the main modification in the illustrated implant fixture lies in the axial opening or hole 43. The geometric limitation on this hole is defined by the implant diameter D and the depth of the inner hole 42. The minimum depth of the hole 43 is preferably not less than 1.5×the hole diameter. However, a factor of 1.25 is used in many successful clinical cases.

A modification of the implant fixture according to FIG. 6 permits a body or support for growth factors to be fitted in the axial hole 43 of the implant body part. FIG. 2 shows such a support in the form of a sponge, and FIG. 8 shows the implant fixture according to FIG. 6 when the sponge has been fitted in it. In this particular example of the invention, an absorbent collagen sponge 45 has been used as support. Such a sponge has an elastic, porous mass and absorbs the said biological substance. In the case shown, the sponge has a thickness of 4 mm and a circular configuration with a diameter $d_{sp}$ of approximately 3.1 mm. It can be easily fitted in the axial hole 43 by hand or using a suitable instrument.

Collagen sponge materials in the form of bands, strips, blades or the like with different thicknesses and qualities are available on the market. A punch (not shown) is used to make bodies from the sponge material, in this case circular units with a diameter matching the diameter d of the axial hole 43.

The collagen part is fitted by hand into the hole 43 of diameter 3 mm in the implant body. A number of tests have been carried out to obtain reliable fixing of the sponge, in which tests the sponge was either dry or saturated with bioactive substance. These tests showed that the diameter $d_{sp}$ ought to be in the range of 3.0 mm $<d_{sp}>$3.2 mm, both in the dry state and in the wet state.

The secure fixing of the sponge thus makes it possible for liquid containing growth factors to be added to the sponge after the latter has been fitted in the axial hole 43. The modified design of the implant makes it possible to release growth factors through the three holes or openings shown, namely the axial opening 43 and the two perpendicular openings 44. In accordance with the chosen terminology used in the attached patent claims, the recess or hole 43 constitutes an inner space for the body or support. The outer part of the space 43 can be regarded as constituting a channel adjacent to the actual space. In the present case according to FIG. 8, the body or support 45 thus fills both the inner space and the recess or channel in question.

As the growth factors are released to the surrounding bone or surrounding tissue in accordance with the above, it stimulates bone growth or bone growth introduction in the area of the implant. As the collagen sponge is absorbable in itself, it is replaced by newly formed bone within the implant during the absorption process.

As regards the growth factors or the biological substances, these are applied to the sponge in the form of a liquid. A conventional injection instrument or hand pump instrument can be used to apply the desired quantity of liquid to the sponge. As regards the BMP mentioned earlier, this is a human protein which stimulates bone growth and is an example of the growth factors which can be used in the present invention. In particular, it is possible to use known growth factors of the types BMP 2 and BMP 4 which have been identified by the Genetics Institute INC as being suitable in this case. Suitable doses can be obtained from combined systems of implants and sponges with added substance, depending on the status of the bone in the implantation site, which can vary considerably from one case to another. Different concentrations of substance can be applied to the sponge in order to effect a considerable increase in bone growth in the area of the implant.

As regards the structure of the modified implant element which has been described thus far, it will be appreciated that instead of two radial holes 44 at right angles to each other, it is also possible to use other configurations of holes or channels which communicate with the axial hole 43 and open out onto the threaded outer surface. In the illustrative embodiment shown, the release of growth factors is more or less concentrated in the area around the pointed part of the implant body. In the case of an implant element without the said threaded upper hole for a tightening screw, i.e. an implant element which is designed for an external tightening means, or with only a short hole 42, the axial hole 43 can be made much deeper and can extend through the head part of the longitudinal implant body. In such a case, the growth factors can be released along the length of the implant element, through a suitable number of holes or channels 46 in the wall of the implant element (see FIG. 9). Alternatively, the sponge support can also be designed as a rod, or one or more sponge strips can be fitted in such a longitudinal hole or in the channel itself.

The invention is not limited to the embodiment described above by way of example, and instead it can be modified within the scope of the attached patent claims and the inventive concept. Thus, for example, the invention is not limited to the bodies or supports in the embodiment described above. Supports in the form of gels, solid bodies, liquids or the like can be used, provided that their dimensions and/or the viscosity permits fixing to the implant configuration in question. In the illustrative embodiment, a standard fixture has been modified in order to permit insertion of a suitable support for bioactive substances, in order to obtain a combination of implant and support which permits advantageous release of the bioactive substances into the tissue surrounding the implant element.

What is claimed is:

1. A method for using an implant element for delivering at least one bioactive substance to bone or tissue structure surrounding an implant, comprising:

providing an implant element comprising:
   a head part arranged to be acted upon by a turning tool,
   a threaded outer surface, and
   a conical tip opposite the head part;
providing an open section in the conical tip, wherein the open section comprises an axial hole that is open towards an end surface of the conical tip, and wherein the open section comprises at least one radial through-hole which communicates with the axial hole and extends radially through the implant element to the outer surface of the implant element;

providing at least one body in the open section, wherein the at least one body is arranged to permit direct release of the at least one bioactive substance from the body to the bone or tissue structure through the axial hole and the at least one radial through-hole;

and applying the at least one bioactive substance to the at least one body before or after providing the at least one body in the open section.

2. An arrangement for an implant for delivering at least one bioactive substance to bone or tissue structure surrounding the implant during at least part of a period of incorporation of the implant in the bone or tissue structure, wherein the arrangement comprises:

an implant element comprising:
 a head part arranged to be acted upon by a turning tool,
 a threaded outer surface, and
 a conical tip opposite the head part, wherein the conical tip comprises an open section, wherein the open section includes an axial hole that is open towards an end surface of the conical tip, and wherein the open section comprises at least one radial through-hole which communicates with the axial hole and extends radially through the implant element to the outer surface of the implant element, and;

at least one body comprising the at least one bioactive substance, wherein the at least one body is disposed in the open section and is arranged to permit direct release of the at least one bioactive substance from the body to the bone or tissue structure through the axial hole and the at least one radial through-hole.

3. Arrangement according to claim 2, wherein the at least one body is in the form of a spongy body or cloth saturated in or treated with the at least one bioactive substance, or a gel which comprises the at least one bioactive substance, and wherein the at least one body has a softness which permits distinct application in the open section while ensuring that the at least one body is held in place by frictional cooperation or adhesive cooperation with an inner wall of the open section.

4. Arrangement according to claim 2, wherein the implant element has clinically effective geometrical properties and has the shape of a cylindrical or conical solid, and wherein the outer surface is arranged for direct contact with the bone or tissue structure.

5. Arrangement according to claim 2, wherein the at least one body comprises an absorbable collagen sponge.

6. Arrangement according to claim 2, wherein the at least one bioactive substance is a substance belonging to the superfamily TGF-13.

7. Arrangement according to claim 2, wherein the axial hole extends from the conical tip through the head part in order to permit release of growth factors along the length of the implant element through a suitable number of channels or recesses in the outer surface of the implant element.

8. Arrangement according to claim 2, wherein the design and structure of the at least one body are chosen on the basis of predetermined release functions.

9. Arrangement according to claim 2, wherein the at least one body comprises a first body and a second body, and wherein the first body assumes a first position in which the first body is arranged with a first degree of exposure of a certain substance, and the second body assumes a second position in which the second body has a second degree of exposure of the certain substance, or of another substance, less than the first degree of exposure, for the purpose of permitting a controlled or optimum release function in a particular implant application.

10. Arrangement according to claim 2, wherein the at least one body is arranged in such a way that, in a cooperation and release function, the at least one body varies a degree of release of the at least one bioactive substance, and effects a greater degree of release at a start of a release period than at an end of a release period or effects a greater degree of release at an end of a release period than at a start of a release period.

11. Arrangement according to claim 2, wherein the design or extent of the axial hole and the at least one radial through-hole are chosen on the basis of a predetermined or anticipated release function.

12. Arrangement according to claim 2, wherein the axial hole and the at least one radial through-hole are arranged with different cross-sectional areas or extents, such that different parts of a body or different bodies among the at least one body are subject to different degrees of exposures in a release function, for the purpose of permitting a controlled or optimum release function for the at least one bioactive substance.

13. Arrangement according to claim 2, wherein the at least one body comprises two bodies situated at a distance from each other in order to serve different parts of the bone or tissue strucutre.

14. Arrangement according to claim 2, wherein the implant element and the at least one body can be built up or chosen from a number of implant elements which vary with respect to the axial hole and the at least one radial through-hole or from a number of different bodies having different properties with respect to release function and the at least one bioactive substance.

15. Arrangement according to claim 2, wherein the at least one body can be introduced into the open section and, after introduction, can be saturated with bioactive substance by means of an injection needle or a hand pump.

16. Arrangement according to claim 3, wherein the implant element has clinically effective geometrical properties and has the shape of a cylindrical or conical solid, and wherein the outer surface is arranged for direct contact with the bone or tissue structure.

17. Arrangement according to claim 3, wherein the at least one body comprises an absorbable collagen sponge.

18. Arrangement according to claim 4, wherein the at least one body comprises an absorbable collagen sponge.

* * * * *